(12) United States Patent
Howat

(10) Patent No.: US 8,475,431 B2
(45) Date of Patent: Jul. 2, 2013

(54) INTRODUCER SHEATH HAVING A BRAIDED MEMBER AND METHODS OF MANUFACTURE

(75) Inventor: William L. Howat, Laconia, NH (US)

(73) Assignee: Cook Medical Technologies LLC, Bloomington, IN (US)

( * ) Notice: Subject to any disclaimer, the term of this patent is extended or adjusted under 35 U.S.C. 154(b) by 675 days.

(21) Appl. No.: 12/176,020

(22) Filed: Jul. 18, 2008

(65) Prior Publication Data

US 2010/0016837 A1    Jan. 21, 2010

(51) Int. Cl.
*A61M 25/00*    (2006.01)

(52) U.S. Cl.
USPC .......................................... 604/527; 604/526

(58) Field of Classification Search
USPC ......... 604/523–532, 164.01–164.09; 156/143
See application file for complete search history.

(56) References Cited

U.S. PATENT DOCUMENTS

| | | | |
|---|---|---|---|
| 3,585,707 A | 6/1971 | Stevens | |
| 5,380,304 A | 1/1995 | Parker | |
| 5,545,208 A | 8/1996 | Wolff et al. | |
| 5,702,373 A * | 12/1997 | Samson | 604/527 |
| 5,968,091 A | 10/1999 | Pinchuk et al. | |
| 6,030,371 A | 2/2000 | Pursley | |
| 6,562,022 B2 | 5/2003 | Hoste et al. | |
| 6,786,919 B1 | 9/2004 | Escano et al. | |
| 6,887,266 B2 | 5/2005 | Williams et al. | |
| 6,939,337 B2 * | 9/2005 | Parker et al. | 604/528 |
| 6,979,348 B2 | 12/2005 | Sundar | |
| 7,141,061 B2 | 11/2006 | Williams et al. | |
| 2001/0034514 A1 | 10/2001 | Parker | |
| 2009/0299333 A1 * | 12/2009 | Wendlandt et al. | 604/527 |

FOREIGN PATENT DOCUMENTS

WO    WO 2006020044 A1 *    2/2006

OTHER PUBLICATIONS

Printout of website http://cookmedical.com/di/dataSheet.do?id=269 printed Jun. 26, 2008.

* cited by examiner

*Primary Examiner* — Kevin C Sirmons
*Assistant Examiner* — Imani Hayman
(74) *Attorney, Agent, or Firm* — Brinks Hofer Gilson & Lione

(57) ABSTRACT

The present embodiments provide an introducer sheath having a braided member and methods of manufacture. The introducer sheath comprises an inner tube, a braided member disposed over at least a portion of the inner tube, and an outer tube disposed over the inner tube and the braided member. In one embodiment, the braided member comprises a plurality of intersecting first and second wire segments at least partially covered with a coating. At least a portion of the first and second wire segments are bonded together at one or more intersections, for example, by melting the coating, to reduce movement of at least one of the first and second wire segments with respect to one another. Optionally, a coiled member having a plurality of turns may be disposed over a portion of the braided member and the inner tube.

7 Claims, 4 Drawing Sheets

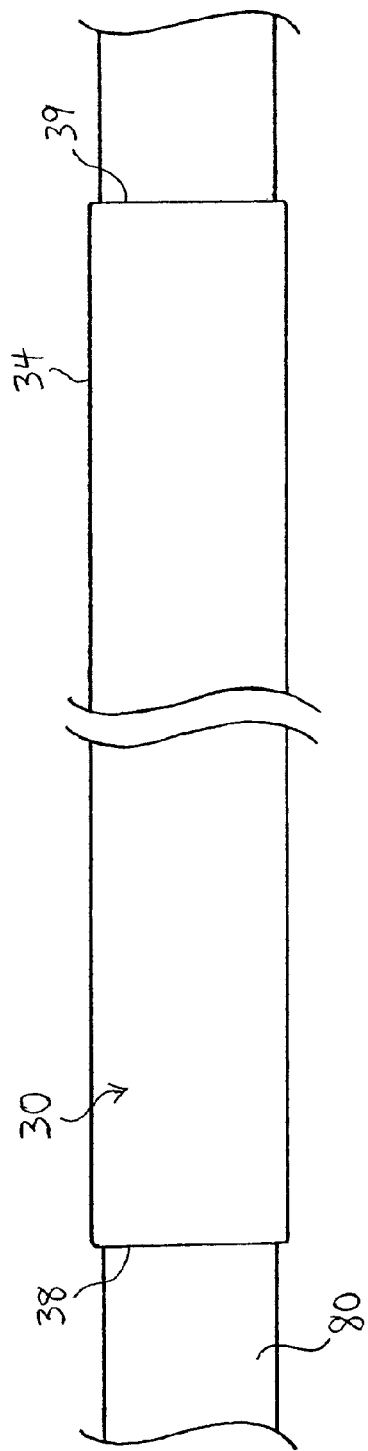
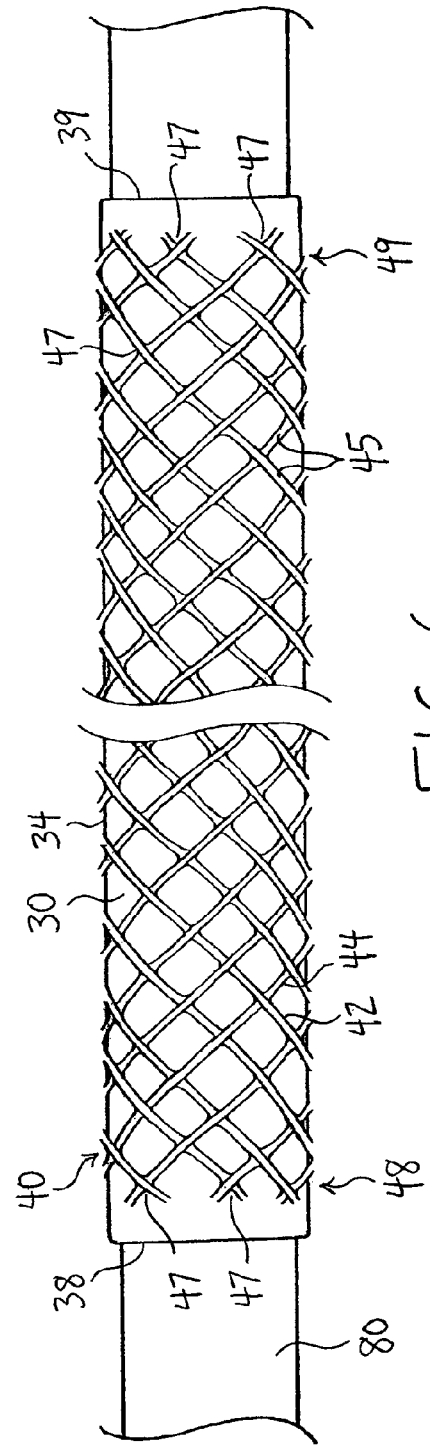

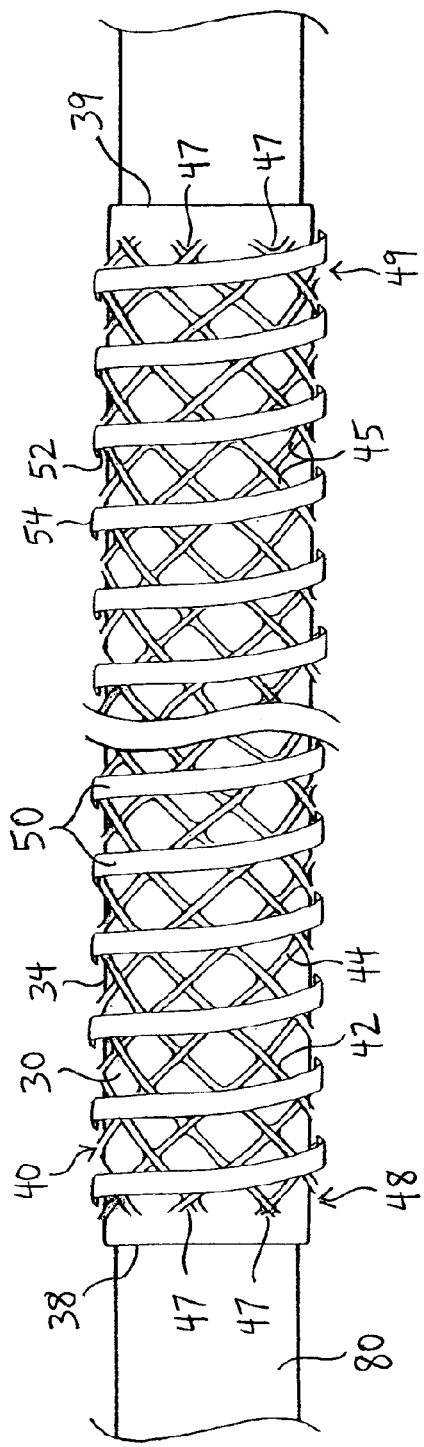
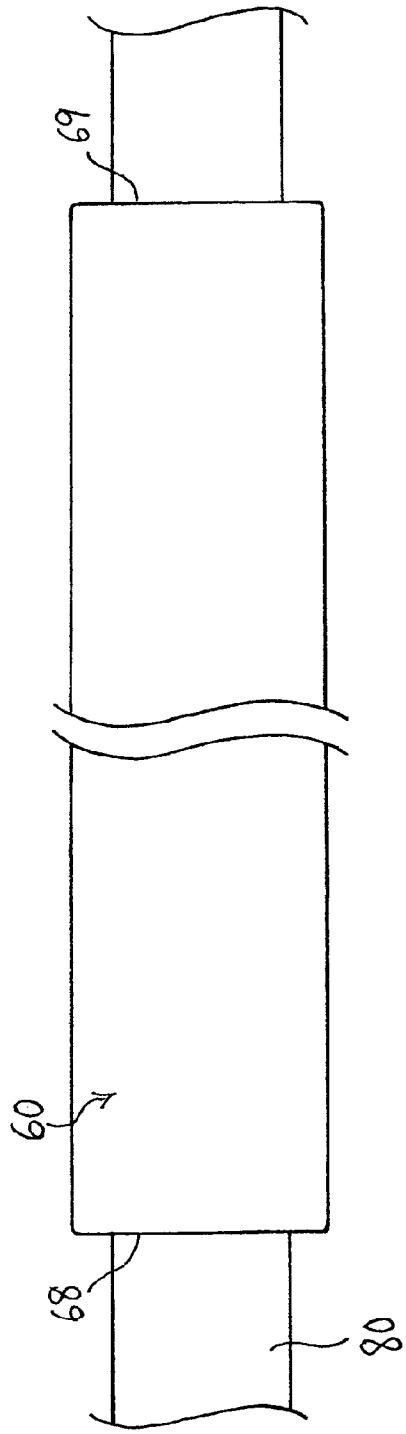
FIG. 7
FIG. 8

INTRODUCER SHEATH HAVING A BRAIDED MEMBER AND METHODS OF MANUFACTURE

BACKGROUND

The present embodiments relate generally to the field of medical devices, and more particularly, to an introducer sheath having a braided member.

Introducer sheaths are well-known for percutaneous vascular access and may comprise a suitable material such as polytetrafluoroethylene or fluorinated ethylene propylene. Such sheaths may comprise a relatively thin-wall construction, but may tend to kink. Increasing the thickness of the sheath wall minimally improves the level of kink resistance, which is still unacceptable. While positioned in a patient, the sheath may be bent or pinched off. A kinked sheath is unusable and cannot be straightened while positioned inside the body of a patient. Consequently, the sheath must be removed. Vascular access is then attempted at an alternative site, and the procedure is restarted, which causes an unacceptable time delay. Moreover, in some cases, an alternative site is not available for introducing another sheath.

One introducer sheath with improved kink resistance is disclosed in U.S. Pat. No. 5,380,304 to Parker (hereinafter "the '304 patent"). The introducer sheath comprises a coil having a plurality of turns, which is positioned around an inner tube. An outer tube is connected to the inner tube through the uniform spacing of the coil turns. As a result, the coil of the '304 patent reinforces the wall to provide an extremely kink-resistant and thin-walled introducer sheath. Preferably, the coil comprises a flat wire for minimizing the wall thickness of the sheath.

At least one other introducer sheath on the market has employed a braided member, which is disposed between inner and outer tubes of the sheath. The provision of a braided member advantageously may improve the overall torqueability characteristics of the introducer sheath. However, braided members typically are difficult to cut to length since the filaments may move with respect to one another, leading to partial unraveling and/or foreshortening. Moreover, the ends of the braided members may tend to flare in a radially outward direction, thereby causing difficulties in the assembly and manufacture of the introducer sheath.

SUMMARY

The present embodiments provide an introducer sheath having a braided member, along with exemplary methods of manufacture. The introducer sheath comprises an inner tube, a braided member disposed over at least a portion of the inner tube, and an outer tube disposed over the inner tube and the braided member. In one embodiment, the braided member comprises a plurality of intersecting first and second wire segments. At least a portion of the first and second wire segments are bonded together at one or more intersections to reduce movement of the first and second wire segments with respect to one another.

In one embodiment, at least a portion of an outer surface of the first and second wire segments are covered with a coating. During manufacture, at least a portion of the first and second wire segments may be bonded together at one or more of the intersections, for example, by melting the coating, thereby reducing movement of the first and second wire segments with respect to one another. This may promote a localized tacking of the first and second wire segments together, particularly at the bonded intersections. The localized tacking may allow proximal and distal ends of the braided member to be cut to a desired length without substantial radial flaring of the first and second wire segments.

Optionally, a coiled member having a plurality of turns may be disposed over a portion of the braided member and the inner tube. In this embodiment, the outer tube is disposed over the inner tube, the braided member and the coiled member. If the first and second wire segments of the braided member are tacked or bonded together at one or more intersections, manufacturing of the introducer sheath may be simplified because it may be easier to position the coiled member and/or the outer tube over the stabilized braided member.

In one manufacturing step, the outer tube may be heat shrunk between spaces of the coiled member and the braided member, such that at least a portion of the outer tube engages the outer surface of the inner tube. The outer surface of the inner tube may be chemically etched to facilitate a mechanical connection to the outer tube, which may comprise a heat-formable polyamide material. During the heat shrinking process, the coating on the first and second wire segments of the braided member may become at least partially bonded to the inner tube.

Other systems, methods, features and advantages of the invention will be, or will become, apparent to one with skill in the art upon examination of the following figures and detailed description. It is intended that all such additional systems, methods, features and advantages be within the scope of the invention, and be encompassed by the following claims.

BRIEF DESCRIPTION OF THE DRAWINGS

The invention can be better understood with reference to the following figures and description. The components in the figures are not necessarily drawn to scale, emphasis instead being placed upon illustrating the principles of the invention. Moreover, in the figures, like referenced numerals designate corresponding parts throughout the different views.

FIGS. 5-8 are side views of exemplary method steps used to manufacture the introducer sheath of FIG. 1.

DETAILED DESCRIPTION OF THE PREFERRED EMBODIMENTS

In the present application, the term "proximal" refers to a direction that is generally towards a physician during a medical procedure, while the term "distal" refers to a direction that is generally towards a target site within a patient's anatomy during a medical procedure.

Figure 1:
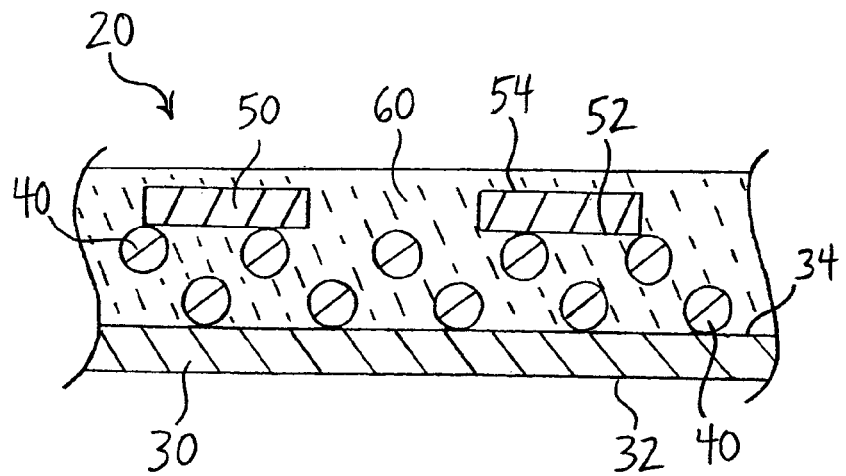
FIG. 1 is a side-sectional view of a portion of an introducer sheath comprising a braided member.

Referring now to FIG. 1, a side-sectional view of a portion of an introducer sheath 20 is shown. In this embodiment, the introducer sheath 20 comprises an inner tube 30, a braided member 40, a coiled member 50 and an outer tube 60. The relationship of the elements of the introducer sheath 20 are explained in further detail below, along with techniques for manufacturing the introducer sheath 20.

The inner tube 30 may comprise a suitable length of a lubricous material tube such as polytetrafluoroethylene ("PTFE"). The inner tube 30 may comprise a uniform inside diameter having dimensions suitable for a particular procedure, for example, in the range of about 0.079 inches to about 0.315 inches. The lubricous PTFE material may provide a relatively slippery inner surface 32 for the easy insertion and withdrawal of a dilator, as well as other catheters and medical apparatus. The inner surface 32 of the inner tube 30 also may be smooth and nonporous for minimizing the formation of blood clots and other thrombi thereon.

An outer surface 34 of the inner tube 30 may be chemically etched in a well-known manner for forming a rough outer surface to which the outer tube 60 may be mechanically connected using a well-known heat shrinking and formation process. Such a technique is explained in greater detail below, as well as in the '304 patent, which is hereby incorporated by reference in its entirety.

The braided member 40 may comprise one or more wires, or wire segments, that are formed into a desired braided pattern and disposed around the outer surface 34 of the inner tube 30. The braided member 40 may comprise a suitable material, such as stainless steel or a shape-memory material such as nitinol, as explained in further detail below. The provision of a braided member 40 between the inner tube 30 and the outer tube 60 may improve the overall torqueability characteristics of the introducer sheath 20.

Figure 2:
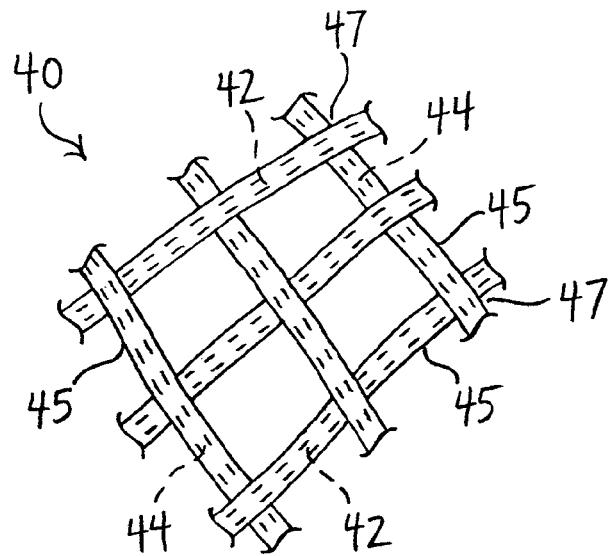
FIG. 2 is a perspective view of a braided member.

The braided member 40 may be braided into any desired pattern, for example, as shown in FIG. 2 below. In this example, the braided member 40 comprises a plurality of first wire segments 42 extending in a first direction and a plurality of second wire segments 44 extending in a second direction. The plurality of first wire segments 42 intersect the plurality of second wire segments 44 at intersections 47, as shown in FIG. 2, to form the braided pattern. Additional features of the braided member 40 are explained in further detail below.

The coiled member 50 may comprise a plurality of flat wire turns, preferably having uniform spacing, and may be formed generally in accordance with a flat wire coil described in the '304 patent. The coiled member 50 may be formed from a flat rectangular stainless steel wire having a thickness of about 0.003 inches and a width of about 0.012 inches. The coiled member 50 may be wound to a diameter slightly greater than an outer diameter of the braided member 40.

The outer tube 60 may comprise a heat-formable polyamide material, such as nylon. The outer tube 60 may comprise an inside diameter configured to be heat shrunk over the coiled member 50 and the braided member 40, as explained in further detail below. The outer tube 60 may be heated and compressed through the spaces between the wire segments of the braided member 40 and the turns of the coiled member 50 with a heat shrink tube for mechanically connecting to the roughened or etched outer surface 34 of the inner tube 30. After the outer tube 60 is heat shrunk onto the outer surface 34 of the inner tube 30, the shrink tube is removed therefrom, and a taper is formed at the distal end of the introducer sheath 20, as explained in further detail in the '304 patent, as well as U.S. Patent Publication No. 2001/0034514 (hereinafter "the '514 publication"), each of which are hereby incorporated by reference in their entirety. It will be appreciated that the final thickness and outer diameter of the introducer sheath 20, including the inner tube 30, the braided member 40, the coiled member 50, and outer tube 60, may be varied and tailored depending on a patient's anatomy and/or the procedure being performed.

Figure 3:
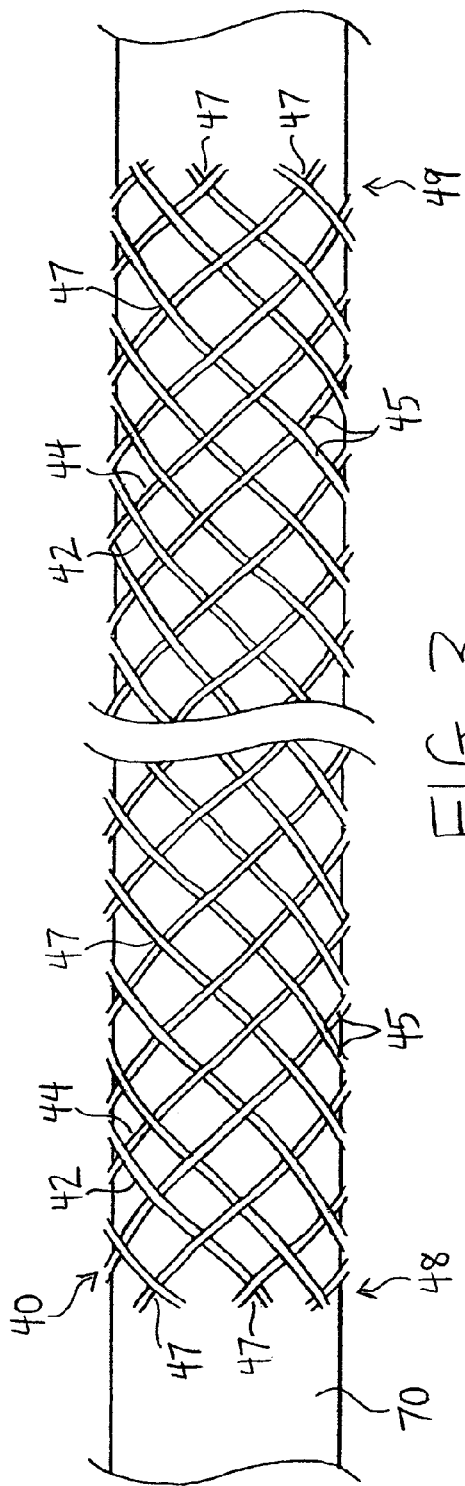
FIG. 3 is a side view of the braided member of FIG. 2 disposed over a mandrel.
Figure 4:
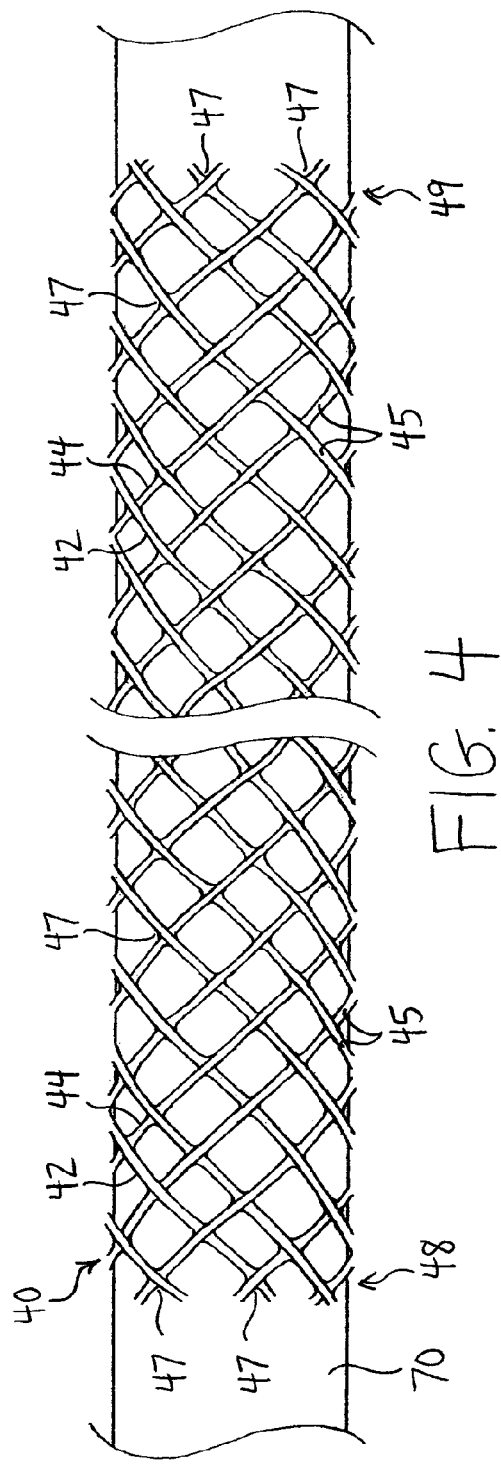
FIG. 4 is a side view of the braided member of FIG. 3 after treatment.

Referring now to FIGS. 2-4, an exemplary braided member 40 is described in further detail. In the embodiment of FIG. 2, each first wire segment 42 passes above two second wire segments 44, then below two second wire segments 44, and may repeat this pattern along the length of the braided member 40. Similarly, each second wire segment 44 passes above two first wire segments 42, then below two first wire segments 42, and may repeat this pattern along the length of the braided member 40, as depicted in FIGS. 2-4. However, in an alternative embodiment, each first wire segment 42 may pass over only one second wire segment 44, then under a next second wire segment 44, and continue to alternate in an over-and-under manner at each intersection 47. Still further braided patterns are contemplated and within the scope of the present invention.

In accordance with one aspect, the braided member 40 comprises a portion having a coating 45. The coating 45 may comprise any suitable material, including but not limited to thermoplastics, such as those in the nylon and urethane families, for manufacturing purposes explained further below.

At least a portion of an outer surface of one or more first wire segments 42 may be covered with the coating 45, and at least a portion of an outer surface of one or more second wire segments 42 may be covered with the coating 45. Preferably, the entire outer surfaces of the first and second wire segments 42 and 44 are coated with the coating 45, i.e., such that the coating 45 substantially encircles the first and second wire segments 42 and 44 and generally conforms to a finished, braided pattern of the braided member 40. This may be achieved using any suitable technique, including spraying the coating 45 onto the first and second wire segments 42 and 44, or dipping one or more wire segments into a batch of the coating 45. Alternatively, only selected portions of the first and second wire segments 42 and 44 may be covered with the coating 45, for example, in the vicinity of one or more selected intersections 47.

Once the first and second wire segments 42 and 44 of the braided member 40 are partially or fully covered with the coating 45, the wire segments may be braided onto a suitable mandrel 70 to form the desired overall braided pattern, as shown in FIG. 3. In one embodiment, an inert mandrel, such as a glass mandrel, may be employed, wherein the mandrel 70 has an outer diameter that is approximate or slightly less than a desired inner diameter of the braided member 40.

In a next step, at least a portion of the first and second wire segments 42 and 44 are bonded together at one or more of the intersections 47 to reduce movement of at least one of the first and second wire segments 42 and 44 with respect to one another. The bonding may be achieved in various manners, including but not limited to thermal, mechanical and chemical techniques.

In an example of a thermal bonding technique, the mandrel 70, with the braided member 40 disposed thereon, may be passed through a heat source to permit the coating 45 to at least partially melt, as depicted in FIG. 4. Accordingly, one or more of the intersecting first and second wire segments 42 and 44 may be thermally bonded together at one or more intersections 47, thereby at least partially limiting movement of the intersecting wire segments 42 and 44 with respect to one another. Preferably, the coating 45 of a first wire segment 42 is lightly bonded or "tacked" to the coating 45 of a second wire segment in the vicinity of the intersection 47, as opposed to rigidly fused together.

By way of example, the heat source used to melt the coating 45 may employ convection, radiant, or radiofrequency heating techniques. If the coating 45 comprises a thermoplastic such as nylon, the nylon may melt when exposed to an appropriate temperature, for example, between 300-500 degrees Fahrenheit, depending on the particular melting point of the material.

If the first and second wire segments 42 and 44 of the braided member 40 comprise a shape-memory alloy, such as nitinol, then preferably the melting process of the coating 45 does not affect the integrity or characteristics of the shape-memory alloy. For example, if the wire segments 42 and 44 comprise nitinol, then the temperature used to heat and melt the coating 45 preferably does not exceed a threshold, such as 700 degrees Fahrenheit, which may otherwise affect the shape-memory properties of nitinol.

In other examples, the bonding of the first and second wire segments 42 and 44 may be achieved using mechanical techniques. For example, the coating 45 may comprise putty-like characteristics. When the braided member 40 is disposed around the mandrel 70 and mechanically compressed, the coating on a first wire segment 42 may become bonded or "tacked" to the coating on a second wire segment 44 at one or more of the intersections 47, thereby reducing movement of at least one of the first and second wire segments 42 and 44 with respect to one another. Alternatively, a non-thermal, chemical substance may be applied to portions of the first and second wire segments 42 and 44 to bond the wire segments together at one or more of the intersections 47.

In accordance with one aspect, proximal and distal ends 48 and 49 of the braided member 40 may be at least temporarily held in place by the bonding of the coating 45 and the subsequent tacking of the intersections 47 together. In effect, the first and second wire segments 42 and 44 may be less inclined to flare in a radially outward direction near the proximal and distal ends 48 and 49 of the braided member 40. The braided member 40 subsequently may be cut to a desired length, and the ends of the wire segments 42 and 44 will be less likely to flare radially outward due to the tacking of the wire segments 42 and 44 at the intersections 47. This feature may provide a significant advantage during the manufacture of the introducer sheath 20.

Referring now to FIGS. 5-8, exemplary method steps are described for manufacturing the introducer sheath 20 of FIG. 1. In a first step, the inner tube 30 may be placed over a mandrel 80. The mandrel 80 has an outer diameter that is approximate or slightly less than a desired inner diameter of the inner tube 30.

The braided member 40, with one or more intersections 47 bonded together as described in FIGS. 3-4 above, then may be advanced coaxially over the outer surface 34 of the inner tube 30. In one exemplary technique, the mandrel 70 of FIGS. 3-4, having the braided member 40 disposed thereon, may be aligned with an end of the mandrel 80. The braided member 40 then may be transferred from the mandrel 70 directly over the inner tube 30. The braided member 40 may be positioned such that the proximal and distal ends 48 and 49 of the braided member 40 are positioned a short distance away from proximal and distal ends 38 and 39 of the inner tube 30, respectively, as shown in FIG. 6.

Referring to FIG. 7, in a next step the coiled member 50 may be fitted around the braided member 40 and the inner tube 30. Like the braided member 40, proximal and distal ends of the coiled member 50 may be positioned a short distance from the proximal and distal ends 38 and 39 of the inner tube 30, respectively, which may permit tapering and flaring of the ends of the introducer sheath 20.

Advantageously, since the braided member 40 is treated as described above, for example, by providing a coating 45 and bonding portions of the coating 45, the first and second wire segments 42 and 44 are less likely to flare radially outward, which may facilitate insertion of the coiled member 50 over the proximal end 48 or distal end 49 of the braided member 40. More specifically, the coiled member 50 has an inner surface 52 and an outer surface 54. The tacking bond of the coating 45 at the intersections 47 may substantially reduce or inhibit radial flaring at the proximal and distal ends 48 and 49 of the braided member 40, after the proximal and distal ends 48 and 49 are cut to a desired length, which may facilitate retention of the braided member 40 at an outer diameter suitable for accommodating the inner surface 52 of the coiled member 50.

With the coiled member 50 positioned over the braided member 40 and the inner tube 30, as shown in FIG. 7, the outer tube 60 then may be advanced coaxially over the coiled member 50, as shown in FIG. 8. Proximal and distal ends 68 and 69 of the outer tube 60 may be substantially aligned with the proximal and distal ends 38 and 39 of the inner tube 30, respectively, as generally depicted in FIG. 8. Once in place, the outer tube 60 may be joined to the roughened outer surface 34 of the inner tube 30 between spacings of the braided member 40 and turns of the coiled member 50.

In a preferred technique, a sleeve of heat shrinkable tubing is placed around the outer tube 60. Heat may be applied at a temperature of about 300-500 degrees Fahrenheit, which is in the processing temperature range of the outer tube material. This causes the outer tube 60 to melt and flow between the spacings of the braided member 40 and the coiled member 50, being urged thereinto by shrinking of the heat shrink sleeve, which is thereafter removed. Such a heat shrink technique is described in greater detail in the '304 patent.

Once the process is completed, the heat shrink tubing may be split from around the outer tube 60, the mandrel 80 may be removed from within the lumen of the inner tube 30, and the introducer sheath 20 is in the form shown from the partial side-sectional view in FIG. 1. Since the heat formable material outer tube 60 also may be self-leveling, it may provide a uniform outer diameter surface for the introducer sheath 20. Subsequently, other manufacturing steps may be employed to complete the construction of the introducer sheath 20, such as thermally bonding a distal tip portion to a distal end 69 of the outer tube 60, as generally set forth in the '304 patent and the '514 publication.

Various technical advantages may be achieved by placing the braided member 40 beneath the coiled member 50. For example, during the heat shrink process, the coating 45 may melt at the heat shrink temperature, which may facilitate bonding of the braided member 40 to the inner tube 30 during manufacture, particularly since the braided member 40 is urged towards the inner tube 30 via the compression of the heat shrink tubing. As another example of a technical advantage, the surface area of the open spacing between wires of the braided member 40 may be greater than the surface area of the open spacing between turns of the coiled member 50, which may provide an increased surface area for directly bonding the outer tube 60 to the inner tube 30 during the heat shrink process. If the bond between the outer tube 60 and the inner tube 30 is enhanced, then the overall structural integrity of the introducer sheath 20 may be improved.

Alternatively, the braided member 40 may be disposed above the coiled member 50 and within the outer tube 60, in which case it may be desirable to increase the spacing between turns of the coiled member 50 to provide an increased area for directly bonding the outer tube 60 to the inner tube 30. However, it will be apparent that the techniques described above to stabilize intersections of the braided member 40 using a coating 45 may be used in any sheath construction having a braided member, regardless of whether the coiled member 50 is used in conjunction with the braided member 40.

While various embodiments of the invention have been described, it will be apparent to those of ordinary skill in the art that many more embodiments and implementations are possible within the scope of the invention. Accordingly, the invention is not to be restricted except in light of the attached claims and their equivalents. Moreover, the advantages described herein are not necessarily the only advantages of the invention and it is not necessarily expected that every embodiment of the invention will achieve all of the advantages described.

I claim:

1. An introducer sheath for use in a medical procedure, the introducer sheath comprising:
   an inner tube having inner and outer surfaces;
   a braided member disposed over at least a portion of the inner tube, wherein the braided member comprises a plurality of first wire segments extending in a first direction and a plurality of second wire segments extending in a second direction, wherein the plurality of first and second wire segments intersect at one or more intersections, and wherein at least one of the first wire segments passes above one second wire segment and below another second wire segment, wherein at least a portion of an outer surface of the first and second wire segments are covered with a coating, wherein the coating follows the shape of the first and second wire segments such that open spaces between the first and second wire segments lack the coating; and
   an outer tube disposed over the inner tube and the braided member.

2. The introducer sheath of claim 1 wherein at least a portion of the first and second wire segments are bonded together, via the coating, to reduce movement of at least some of the first and second wire segments of the braided member with respect to one another.

3. The introducer sheath of claim 2 wherein the coating on the first and second wire segments of the braided member is at least partially bonded to the inner tube.

4. The introducer sheath of claim 1 wherein the outer tube is adapted to be heat shrunk between spaces of the braided member, such that the outer tube engages the inner tube.

5. The introducer sheath of claim 4 wherein the outer surface of the inner tube is chemically etched to facilitate a mechanical connection to the outer tube.

6. The introducer sheath of claim 1 further comprising a coiled member having a plurality of turns disposed over at least a portion of the inner tube and the braided member.

7. An introducer sheath for use in a medical procedure, the introducer sheath comprising:
   an inner tube having inner and outer surfaces;
   a braided member disposed over at least a portion of the inner tube, wherein the braided member comprises a plurality of first wire segments extending in a first direction and a plurality of second wire segments extending in a second direction, wherein the plurality of first and second wire segments intersect at one or more intersections, wherein at least one of the first wire segments passes above one second wire segment and below another second wire segment, wherein at least a portion of an outer surface of the first and second wire segments are covered with a coating;
   an outer tube disposed over the inner tube and the braided member,
   wherein at least a portion of the first and second wire segments are bonded together at one or more of the intersections prior to placement of the outer tube over the braided member, and
   a coiled member having a plurality of turns disposed over at least a portion of the inner tube and the braided member, wherein at least a portion of the first and second wire segments are bonded together at one or more of the intersections prior to placement of the coiled member over the braided member.

* * * * *